United States Patent [19]

Abe et al.

[11] Patent Number: 5,224,948

[45] Date of Patent: Jul. 6, 1993

[54] SUTURING DEVICE FOR MULTIPOSITION HOLDING OF SUTURE NEEDLES

[75] Inventors: Hiroshi Abe, Sapporo; Tomohiko Asahara, Kusatsu, both of Japan

[73] Assignee: Ethicon, Inc., Somerville, N.J.

[21] Appl. No.: 780,601

[22] Filed: Oct. 23, 1991

[30] Foreign Application Priority Data

Oct. 23, 1990 [JP] Japan ............................. 2-110660[U]
Aug. 30, 1991 [JP] Japan ............................. 3-76768[U]

[51] Int. Cl.⁵ ................................................ A61B 17/00
[52] U.S. Cl. ..................................... 606/147; 606/144; 606/145; 606/148
[58] Field of Search ............... 606/139, 144, 145, 146, 606/147, 148

[56] References Cited

U.S. PATENT DOCUMENTS

| | | | |
|---|---|---|---|
| 508,939 | 11/1893 | Hanchett | 606/147 |
| 3,168,097 | 2/1965 | Dormia | 606/147 |
| 3,638,654 | 2/1972 | Akuba | 606/144 |
| 4,621,640 | 11/1986 | Mulhollan et al. | 606/144 |

Primary Examiner—Stephen C. Pellegrino
Assistant Examiner—Jeffrey A. Schmidt

[57] ABSTRACT

The present invention provides a deep suturer suitable for suturing a deep portion and a narrow portion which are difficult to be applied by a normal direct hand operation such as transoral operation. The suturer comprises an end needle-holding portion (B) for holding a suture needle, a holder portion (A) for operating the end needle-holding portion (B) and a connection portion (C) for operatively connect the end needle-holding portion (B) and holder portion (B) is provided with a disk head (4) which is rotated integral with a needle-holding portion (5) the holder portion (A) is provided with a handle (2), and the connection portion (C) is provided with a rod (7) having one end connected to the handle (2) through a connecting mechanism (18) and the other end connected to the disk head (4), the rod (7) being axially slidably inserted by of a spring force.

4 Claims, 7 Drawing Sheets

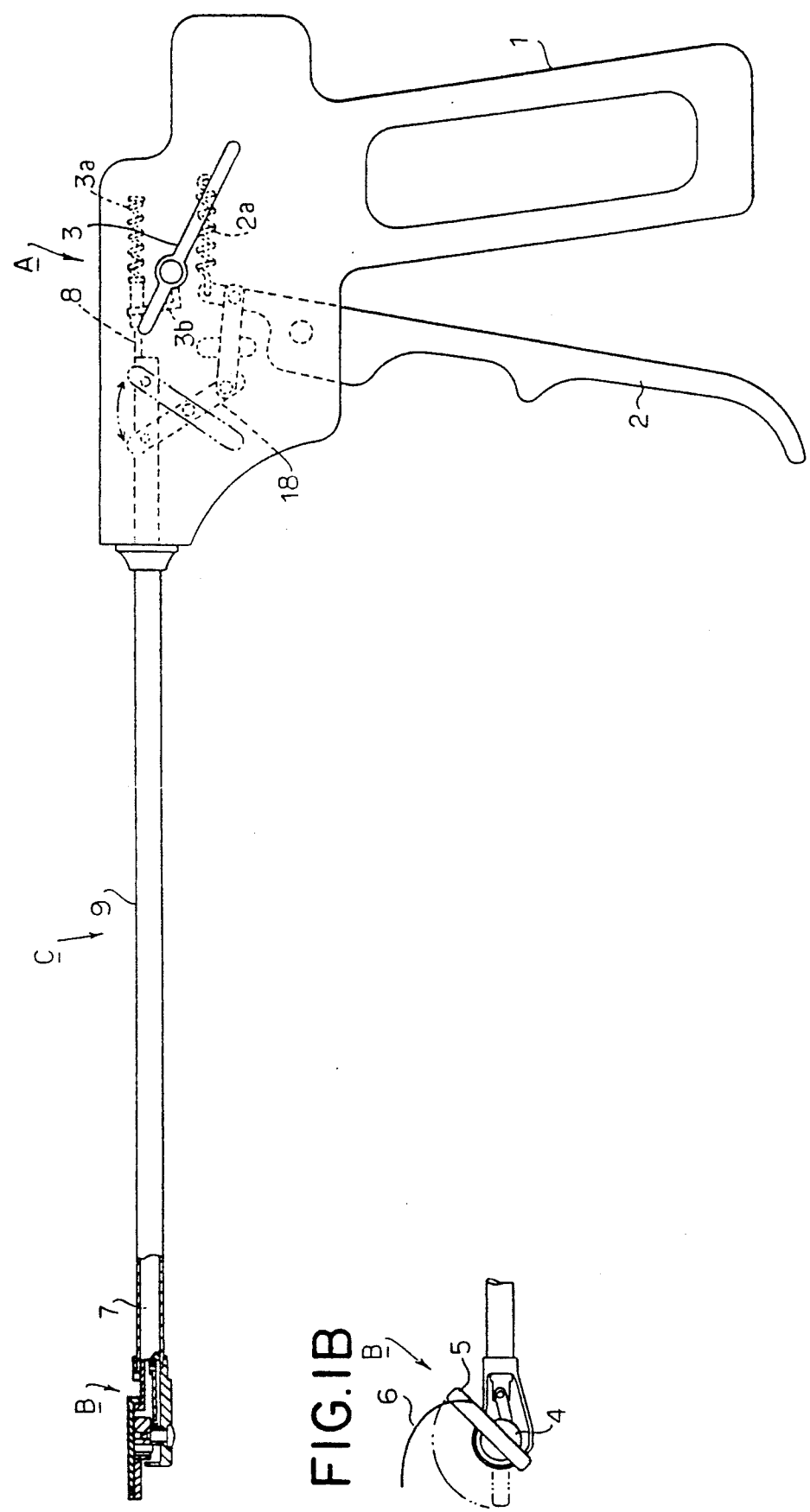

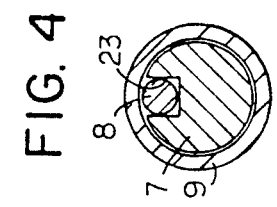
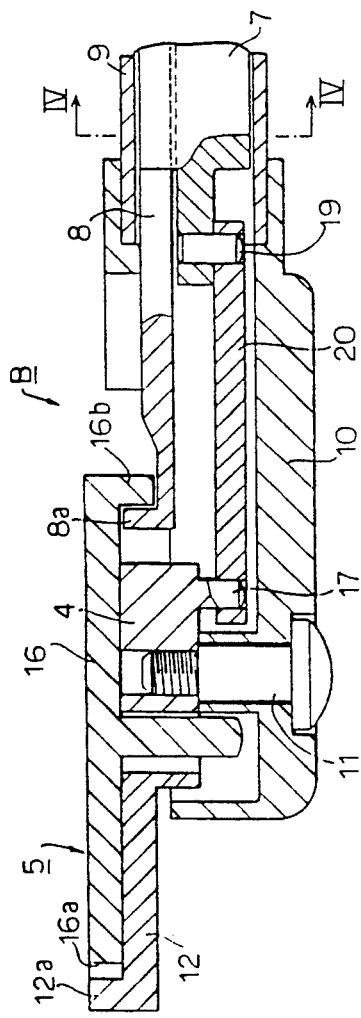
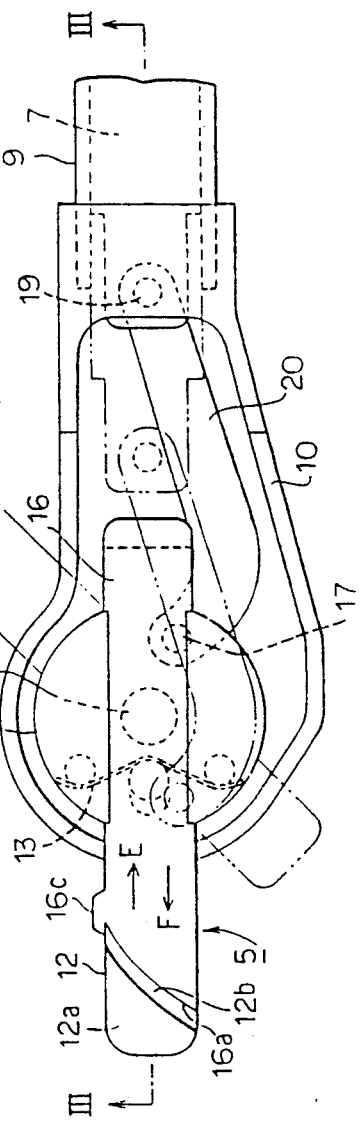

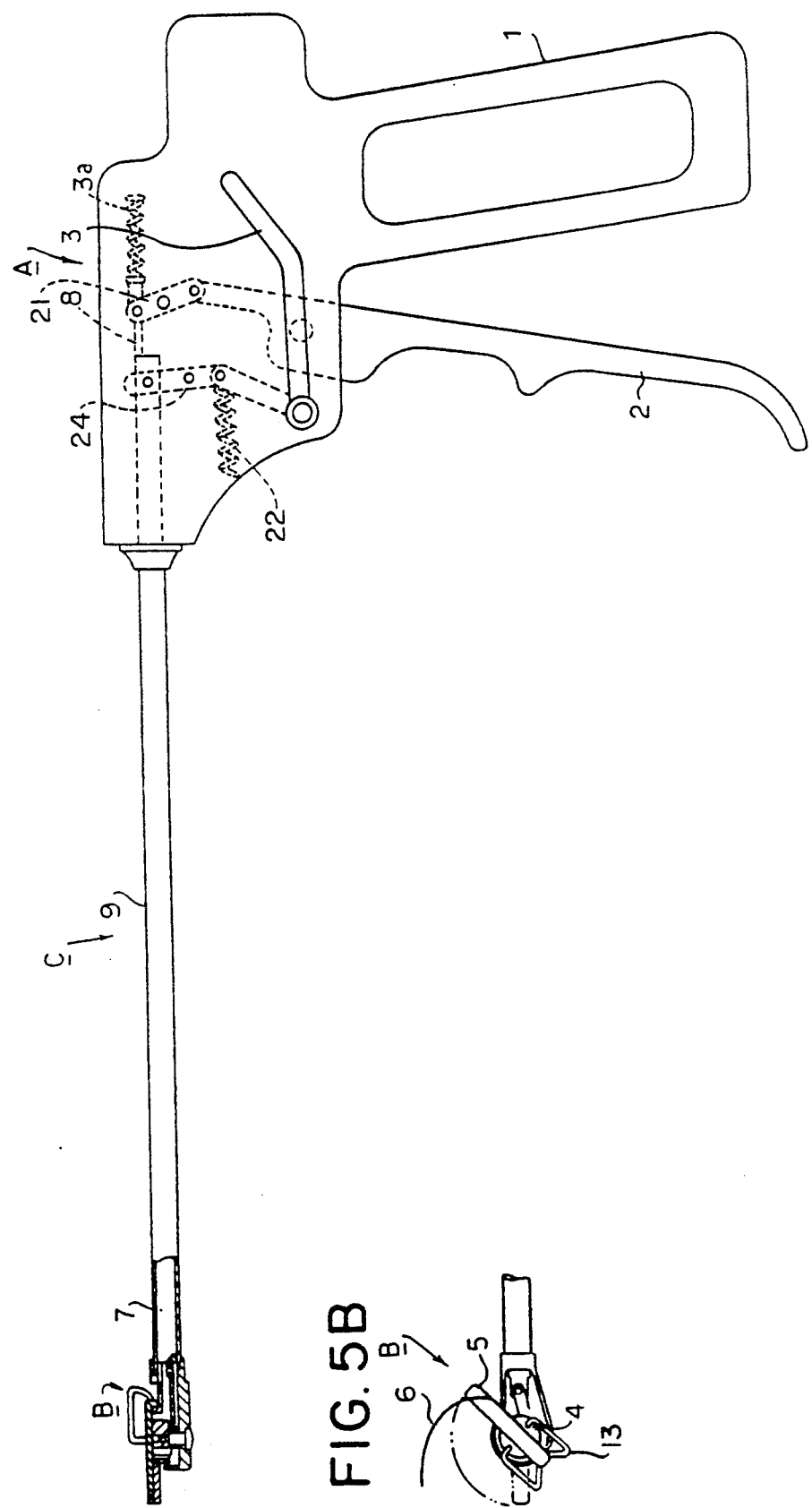

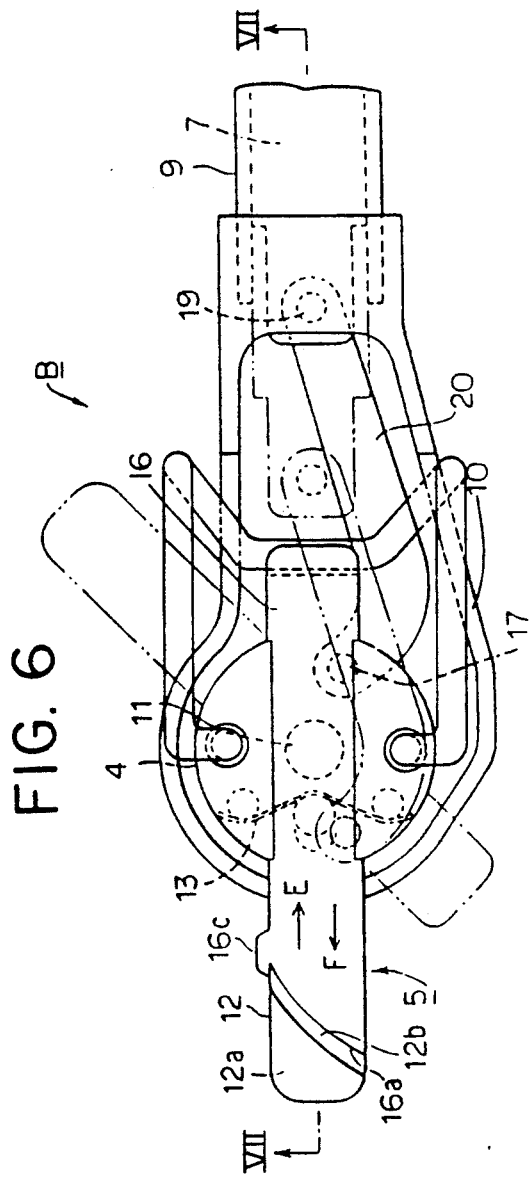

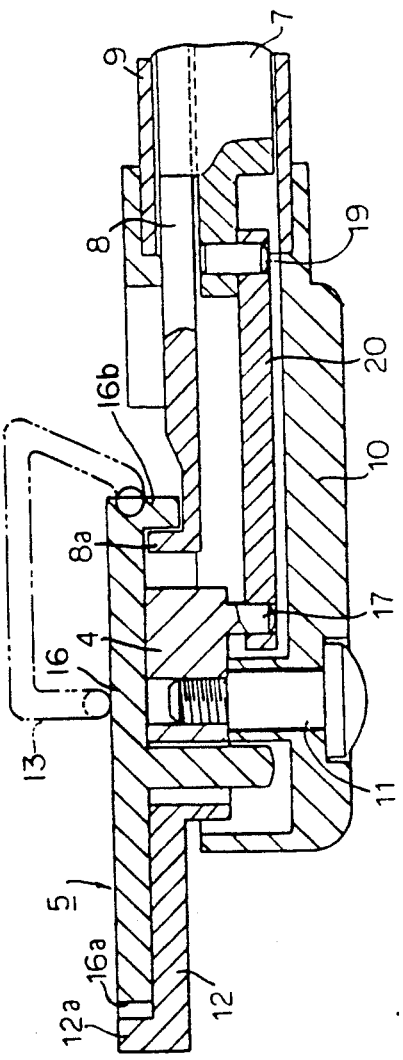

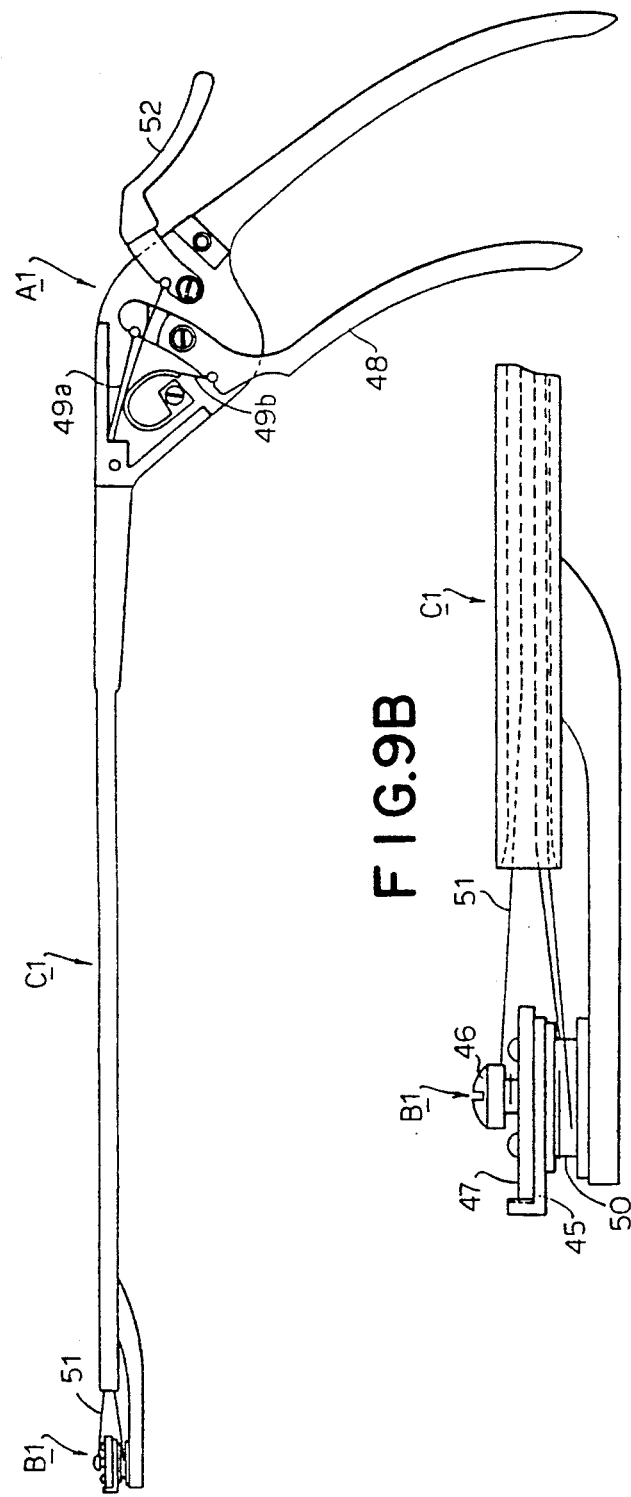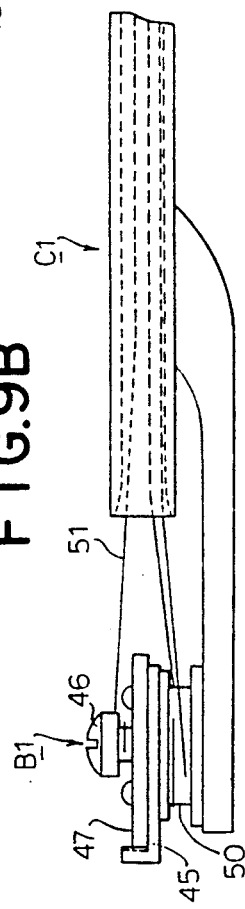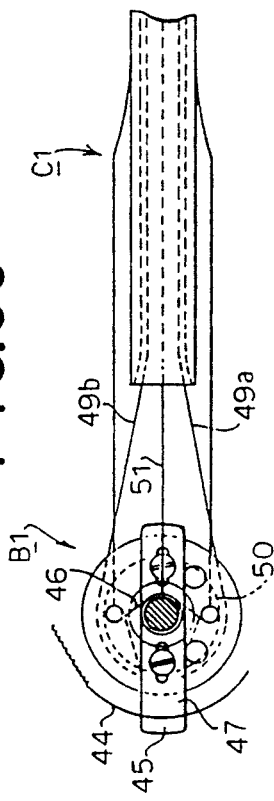

SUTURING DEVICE FOR MULTIPOSITION HOLDING OF SUTURE NEEDLES

This invention relates to a deep suturer suitable for suturing a deep and narrow incision which is difficult to suture by a normal direct hand operation such as transoral operation.

BACKGROUND OF THE INVENTION

A needle holder presently used for suturation has the construction in which a suture needle is held in a direction at right angles to the long axis of the needle holder. Accordingly, suturation is difficult in the field of operation for deep and narrow locations. Some constructions have been proposed in order to solve this problem. However, none of them have yet been commercialized. For example, FIG. 8 and FIG. 9 show conventional deep suturers described in IKIGAKU, Vol. 158, No. 12, p. 531-532 (1988) and Japanese Utility Model Publication No. 62-32006, respectively.

First, the structure and operation of the suturer shown in FIG. 8 will be described. This suturer comprises a head portion B2 for holding a suture needle, a neck portion C2 for rotating the head portion B2 and a body portion A2 for operating the head portion B2 and the neck portion C2. These are operated by a shaft and a gear. First, by turning an operating knob 31, holding portions 36a and 36b for sandwiching the needle therebetween are opened and closed. Next, gears 40a and 40b are rotated in the same direction by engagement of a gear 41, and a pedestal bevel gear 42 on which the holding portions 36a and 36b are integrally mounted is rotated to left and right by rotating the gear 40a or 40b. The change gear 40a is slidably moved axially along a left shaft 39a into engagement with an auxiliary gear 43 meshed with the center gear 41 and changed into a gear train meshed with the right gear 40b through the auxiliary gear 43 and the center gear 41 whereby the rotational direction of the shafts 39a and 39b is reversed to give the pedestal bevel gear 42 a longitudinal rotation. Accordingly, holding and releasing of the needle are effected by turning the operating knob 31 and, next, the gear train in which the gears 40a, 40b, 41 and 43 are meshed is changed whereby lateral rotation and longitudinal bending drive of the holding portions for suturation are rendered free.

A further conventional suturer is shown in FIGS. 9(a), 9(b) and 9(c). This suturer comprises an end needle-holding portion B1 on which a suture needle is mounted, a holding portion A1 having a holder 48 and an intermediate portion C1 for connecting both B1 and A1 at opposite ends thereof. FIGS. 9(b) and 9(c) show the structure of the end needle-holding portion B1. A suture needle 44 is held so as to be sandwiched between a needle receiver 45 and a slide plate 47 which is slidably moved by a spring plate 46. The needle receiver 45 is integrally mounted on a pulley 50 rotated by a handle 48 of the holding portion A1 through wires 49a and 49b and the slide plate 47 is connected to a small handle 52 through a wire 51. By the operation of the handle 48, the suture needle is rotated for suturation through the wires 49a and 49b and the pulley 50 and, by the operation of the small handle 52, the slide plate 47 is slidably moved by the wire 51 against the spring plate 46 to hold and release the suture needle.

There are a number of problems associated with the prior art suturers. First, in the conventional example shown in FIG. 8, the drive portion is composed of a number of gears and shafts and therefore the whole device increases in dimension and cannot be inserted into a narrow incision for operation. Even if it is inserted, the suturing operation is difficult. Further, in the FIG. 9 example, interlocking between the operative handle and the rotation of the suture needle is deviated due to the slip occurring between the wire and the pulley or the sag of the wire, resulting in a difficulty of adjustment of the handle operation. In addition, it is not possible to give the suture needle a sufficient piercing force with respect to hard tissue due to slippage. Another problem is that since the rotational angle of the suture needle is small, about 90°, the depth of the tissue to be sutured becomes shallow, bringing forth a practical limitation.

SUMMARY OF THE INVENTION

An object of the present invention is to provide a suturer which is provided with a slip-free tight connection means between the rotation of the end needle-holding portion and the handle mechanism can give a sufficient piercing force and which can effect the operation for holding and releasing the needle by the left hand alone or by the right hand simultaneously with the handle and the knob (for a right-handed person).

In the suturer according to the present invention a rod for connecting a disk head and a handle through a connecting mechanism is provided on a connection portion such that the disk head is integral with a needle-holding portion of an end needle-holding portion and is rotatable by a handle which is a part of a nearby portion. Preferably, a small diameter rod is provided for connecting the needle-holding portion to a knob of the nearby holder portion through a connecting mechanism. This permits holding and releasing a suture needle of the needle-holding portion.

Advantageously, a small diameter rod is inserted into an axial groove provided in a rod inserted into a pipe forming the connection portion. Preferably, the range of the rotational angle of the disk head is made wide from 90° to 180°. Conveniently, a projection is provided to support a rear end of a suture needle when the latter is held on the holding portion. Preferably, a needle groove for locking the suture needle is inclined between the center line of a needle receiver and the perpendicular direction of the center line.

With the arrangement as described above, according to the suturer of the present invention, the rotational operation of the needle-holding portion is effected by the handle through the rod and therefore rotation without slip and with smooth motion is obtained. In the preferred embodiment, holding and releasing of the suture needle are effected by the knob through the small diameter rod and therefore fingers of the right hand or fingers of the left hand operating the knob are used to merely push the knob whereby easy and positive operation can be attained.

The rotational operation of the needle-holding portion is effected by the knob through the rod and therefore fingers of the right hand or fingers of the left hand operating the knob are used to merely push the knob such that easy and positive operation can be attained and, moreover, smooth rotation without slip and without unevenness is obtained. In one embodiment, holding and releasing of the suture needle are effected by the handle through the small diameter rod and therefore the operation can be made merely by pulling the handle while holding the main holder.

BRIEF DESCRIPTION OF THE DRAWINGS

The invention will be described with reference to the accompanying drawings:

FIG. 1(a) is a side view showing a first embodiment of this invention and FIG. 1(b) is a top view of an end needle-holding portion of FIG. 1(a);

FIG. 2 is a top view of the end needle-holding portion of FIG. 1;

FIG. 3 is a sectional view taken on line III—III of FIG. 2;

FIG. 4 is a sectional view taken on line IV—IV of FIG. 3;

FIG. 5(a) is a side view showing a second embodiment of this invention;

FIG. 5(b) is a top view of an end needle-holding portion of FIG. 5(a);

FIG. 6 is a top view of the end needle-holding portion of FIG. 5;

FIG. 7 is a sectional view taken on line VII—VII of FIG. 6;

FIG. 9(a) is a side view showing a further conventional prior art example;

FIG. 9(b) is a side view of an end needle-holding portion of FIG. 9(a); and

FIG. 9(c) is a top view of FIG. 9(b).

DETAILED DESCRIPTION OF THE PREFERRED EMBODIMENT

Figure 8:
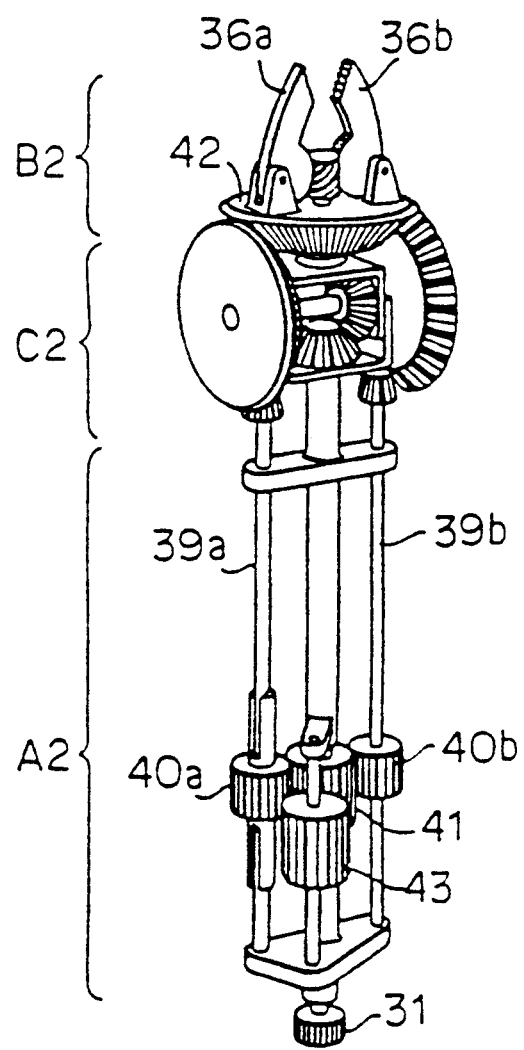
FIG. 8 is a perspective view showing a conventional prior art example.

In the drawings, A denotes a nearby holder portion, B denotes an end needle-holding portion, C denotes a connection portion, 2 denotes a handle, 3 denotes a knob, 4 denotes a disk head, 5 denotes a needle-holding portion, 6 denotes a suture needle, 7 denotes a rod, 8 denotes a small diameter rod, 9 denotes a pipe, 12 denotes a needle receiving bed, 13 denotes a spring plate, 16 denotes a needle locking plate and 23 denotes a groove.

A first embodiment of the present invention will be described with reference to FIGS. 1 to 4 of the drawings.

In FIGS. 1(a) and 1(b), reference character A designates a nearby holder portion gripped by hand for operation, which comprises a main holder 1, a handle 2 having a return mechanism including a spring 2a and a knob 3 having a spring 3a. Reference character B designates an end needle-holding portion which comprises a disk head 4 and a needle-holding portion 5 rotated integral with the disk head 4. Reference character C designates a connection portion, for connection between the nearby holder portion A and the end needle-holding portion B, comprising an operating rod 7 axially slidable within a hollow pipe 9 with a small diameter rod 8 inserted in a groove formed in rod 7.

In FIGS. 2 and 3, an arm bed 10 is fixedly supported on pipe 9 and disk head 4 is rotatably supported on a pin 11 vertically mounted on the arm bed 10. A needle receiver 12 of the needle-holding portion 5 is integrally mounted on one end of the disk head 4. A needle locking plate 16 is provided to be pressed so that an end 16a is placed in contact with a projection 12a of the needle receiver 12 so as to hold the suture needle 6 by means of a plate spring 13 in the form of a resilient body which is slidably moved in directions indicated at arrows E and F within the groove provided in the disk head 4 in an extending direction of the needle receiver 12 on the upper surface thereof.

In order to rotate the disk head 4, a pin 17 is provided at a radial position of the disk head 4 and a link 20 as a connecting mechanism curved into a J-shape so as to avoid contact with pin 11 is rotatably connected to the pin 17 and a pin 19 provided on the end of the rod 7. Rod 7, in turn, is connected to the handle 2 through a connecting mechanism 18.

By this mechanism, the needle-holding portion 5 integral with the disk head 4 is rotated from a position indicated in phantom in FIG. 2 to a position indicated by the solid line in coincidence with the axial direction of the suturer. At the position indicated at the solid line, a hook 16b at the end of the needle locking plate 16 is engaged with a hook 8a at the end of the small diameter rod 8. The small diameter rod 8 is in turn connected to the knob 3 through a connecting mechanism 3b. Actuating the knob 3 causes the needle locking plate 16 to be slidably moved by the small diameter rod 8 through the hooks 8a and 16b against the bias of the spring plate 13. The movement is in a direction indicated by arrow E on the needle receiver 12, whereby the needle groove 12b for holding the suture needle 6 formed between the projecting portion 12a of the needle receiver 12 and the end 16a of the needle locking plate 16 is opened. When the finger is released from the knob 3, the needle groove 12b is closed by the spring force. In this manner, holding and releasing of the suture needle 6 with respect to the needle groove 12b can be effected. In the needle groove 12b, a projection 16c for receiving and supporting the rail portion of the needle is provided integral with the side of the needle locking plate 16 so as to block one end of the needle groove 12b.

In FIG. 4, reference numeral 9 designates a pipe by which the nearby holder portion A and the end needle-holding portion B are connected. Pipe 9 slidably receives a rod 7 having an outer diameter which is smaller than or substantially equal to the inner diameter of the pipe 9. Also slidably received within pipe 9 is a small diameter rod 8 having a circular cross-section so as to be received in an axial slot 23 formed in the upper portion of the rod 7.

The operation of the thus configured suturer of the present invention will be described hereinafter.

First, when the main holder 1 is gripped and the handle 2 is pulled by the finger against the spring force, the rod 7 is pulled and the disk head 4 is rotated counterclockwise, in the figure, through the link 20.

Accordingly, the needle-holding portion 5 integral with the disk head 4 is also rotated counterclockwise and rotated from the position indicated in phantom to the solid line position in FIG. 2. When the direction of the needle-holding portion is coincident with the axis of the rod 7, the hooks 8a and 16b are placed in engagement with each other. Next, when the knob 3 is pushed by the thumb of the right hand against a spring force or rotated by the left hand, the small diameter rod 8 is pulled by the connecting mechanism 3b, and the hooks 8a and 16b are engaged with each other. The needle locking plate 16 is then pulled in a direction as indicated at arrow E by the hooks 8a and 16b against the bias of the spring plate 13. Accordingly, the needle groove 12b formed between the projecting portion 12a of the needle receiving bed 12 and the end 16a of the needle locking plate 16 is opened and the rail portion of the suture needle 6 is placed in the needle groove 12b so that the rail is supported by the projection 16c provided on one end of the needle groove 12b. In this state, when the knob 3 is released, the small diameter rod 8 is returned to its original position by means of the spring force to release engagement between the hooks 8a and 16b. The needle locking plate 16 is also subjected to the biasing force of the spring plate 13 and moves in a direction as indicated at arrow F. The needle groove 12b is closed to lock the suture needle 6. Further, when the handle 2 is pulled and the finger is released, the rod 7 is returned to its original position by means of the spring force. The disk head 4 is then rotated to move the needle-holding portion 5 from the solid-line position to the phantom line position.

After the suture needle 6 has been locked to the needle-holding portion 5 by the operation as described above, that is, when after insertion into the suture portion, the handle 2 is pulled to impart counterclockwise rotation to the needle-holding portion 5 to which the suture needle 6 is locked. The suture needle 6 is mounted at an angle in which the tangential line of the rear end of the needle is inclined at 30° to 80° with respect to the center line of the needle receiving bed 12 and the extreme end thereof is directed outwardly and curved inwardly. Therefore, the rotating suture needle 6 can easily pierce the tissue. Subsequently, in that state, the knob 3 is pushed to release the suture needle 6 from the needle-holding portion 5 to pull out the suturer. Thereafter, the extreme end of the suture needle 6 is held by the needle holder to pull it out of the tissue to complete a stitch of suturation. Similar operation is repeatedly continued.

A second embodiment of this invention will be described hereinbelow with reference to the drawings, in which FIG. 5(a) is a side view showing the entirety of this embodiment, FIGS. 5(b) and 6 are a top view of an end needle-holding portion and FIG. 7 is a sectional view taken on line VII—VII of FIG. 6. This embodiment has the same structure as that of the first embodiment except that a connecting mechanism is connected to the handle 2 and the knob 3 in the first embodiment. Therefore, parts in the second embodiment similar to those of the first embodiment are indicated by the same reference numerals and a description thereof will be omitted.

In FIG. 5, the nearby holder portion A comprises a handle 2 connected through a connecting mechanism 21 to a small diameter rod 8 being applied with a biasing force by means of a spring 3a together with a main holder 1 and a knob 3 connected to a rod 7 through a connecting mechanism 24 having a spring 22 for applying a biasing force.

Accordingly, the suture needle is fixed and when the knob 3 is first turned, the disk head 4 is rotated through the rod 7 by the connecting mechanism 24, similar to the case of the first embodiment, so that the suture is carried out.

Next, when the handle 2 is pulled under the aforesaid state, the needle locking plate 16 is pulled by the small diameter rod 8 from the connecting mechanism 21, similar to the case of the first embodiment, to open the needle groove 12b and release the holding of the suture needle. Thereafter, the needle is pulled out to complete a stitch of suture.

It is convenient that, in order that the main holder 1 may be operated by the thumb of the hand gripping the same, in case of the right-handed person, the mounting position of the knob 3 is set to the left side as viewed from the top and, in the case of the left-handed person, it is set to the right side whereby the operation of the handle and needle holder can be done simultaneously while holding by one hand.

While in the aforementioned embodiment, the small diameter rod 8 has been inserted into the groove 23 provided in the rod 7, it is to be noted that it can be provided externally of the pipe separately from the rod 7.

Preferably, however, it may be inserted into the pipe 9 as in the embodiment in terms of protecting the small diameter rod 8. Alternatively, the pipe 9 may be made to have a slightly larger diameter or to have an egg-like sectional shape, and the rod 7 and the small diameter rod 8 may be juxtaposed and inserted therein.

As the resilient body 13 for pressing the needle locking plate 6 of the needle-holding portion 5 so as to hold the needle 6, a spring plate and a spring rod are provided interiorly and exteriorly in the first and second embodiments, respectively, as shown in FIGS. 6 and 7, but the shape and mounting position of the spring are not limited thereto.

As for the materials used to form the suturer, there can be preferably mentioned those excellent in corrosion resistance, living body adaptability, heat resistance during sterilization and radiation resistance.

As described above, according to the present invention, the rotation of the needle-holding portion of the end needle-holding portion is operated by the handle of the nearby holder portion through the rod. This brings forth effects that: there is no slip in interlocking and positive and tight transmission is obtained; as the case may be, there can be used a large rotational angle close to 180°; and even deep and narrow portions of the tissue to be sutured can be positively sutured.

Moreover, the handle and the knob are provided close to the nearby holder portion whereby the disk head of the needle-holding portion is rotated by either handle or knob through the connecting mechanism and the rod and the needle locking plate of the needle-holding portion is operated to be opened and closed by the other through the connecting mechanism and the small diameter rod. With this arrangement, there provides an effect that the operation of the handle and the knob can be made by fingers of the hand by which the main holder is gripped and the other hand can be used for other operations.

Furthermore, the holding and releasing of the suture needle of the needle-holding portion of the end needle-holding portion is effected by pushing the nearby holder portion connected through the small diameter rod by the finger to rotate it. This also brings further effects that it can be freely operated even by the left hand and that the knob can be operated by the thumb in combination with the handle operation while gripping the main holder by the right hand. Moreover, since the projection for receiving and supporting the tail portion of the suture needle is provided in the needle groove on which the suture needle is mounted, a large piercing force is obtained. The mounting angle of the suture needle is inclined so that the tangential line of the rear end of the needle is in the range of 30° to 80° with respect to the center line of the needle receiving bed and the extreme end of the needle is directed outwardly and curved inwardly. This brings forth the effect that even a deep and narrow tissue can be easily sutured.

We claim:

1. A deep suture device comprising an end needle holding portion for holding a suture needle, a holder portion for operating said end needle holding portion and a connection portion for operatively connecting said end needle holding portion and said holder portion, wherein said end needle holding portion is provided with a disk head which is rotatable, said holder portion is provided with a handle and said connection portion is provided with a rod having one end connected to said handle thorough a connecting mechanism and the other end connected to said disk head through a link, said rod being axially slidable to rotate said disk head, said rod being positioned within a tubular connecting portion which forms part of said connection portion and said rod containing an axial grove along its length which receives therein a smaller diameter rod which is axially slidable within said groove, said smaller diameter rod operatively interconnecting the end needle holder portion and the holder portion to operate said end needle holding portion between a gripping position and anon gripping position for holding a suture needle.

2. A deep suturer according to claim 1 wherein a rotational angle of the disk head of said end needle-holding portion is in the range of 90° to 180°.

3. A deep suturer according to claim 1 wherein a needle groove for holding the suture needle is formed between a projecting end of a needle receiving bed of said needle holding portion and an end of a needle locking plate which is provided with a projection for receiving and supporting a tail portion of the suture needle.

4. A deep suturer according to claim 3 wherein said needle groove is inclined with respect to a center line of the needle-receiving bed.

* * * * *